(12) United States Patent
Bonnet

(10) Patent No.: US 6,482,219 B1
(45) Date of Patent: Nov. 19, 2002

(54) STRICTURE SCALPEL

(75) Inventor: Ludwig Bonnet, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 09/686,255

(22) Filed: Oct. 11, 2000

(30) Foreign Application Priority Data

Nov. 12, 1999 (DE) .......................... 299 19 914

(51) Int. Cl.[7] .............................. A61B 17/32
(52) U.S. Cl. .................... 606/170; 606/167; 30/342; 30/357
(58) Field of Search ............... 606/1, 166, 167, 606/159, 170, 160, 185; 604/272–274; 30/123.7, 272.1, 337, 342, 357, 346, 332, 168, 275.4; 600/104

(56) References Cited

U.S. PATENT DOCUMENTS

| | | | | |
|---|---|---|---|---|
| 3,798,688 A | * | 3/1974 | Wasson | 30/353 |
| 4,485,706 A | * | 12/1984 | Disharoon | 30/350 |
| 4,726,368 A | * | 2/1988 | Morris | 606/151 |
| 4,730,613 A | * | 3/1988 | Gordy | 30/162 |
| 5,055,106 A | * | 10/1991 | Lundgren | 30/321 |
| 5,077,901 A | * | 1/1992 | Warner et al. | 30/346.53 |
| 5,304,190 A | * | 4/1994 | Reckelhoff et al. | 30/134 |
| 5,323,765 A | * | 6/1994 | Brown | 128/898 |
| 5,376,099 A | * | 12/1994 | Ellis et al. | 606/166 |
| 5,529,580 A | * | 6/1996 | Kusunoki et al. | 606/170 |
| 5,665,099 A | * | 9/1997 | Pilo et al. | 30/162 |
| 5,700,274 A | * | 12/1997 | Feaster | 606/167 |
| 5,749,882 A | * | 5/1998 | Hart et al. | 606/159 |
| 5,782,853 A | * | 7/1998 | Zeevi et al. | 30/329 |
| 5,867,912 A | * | 2/1999 | Hickok et al. | 279/46.4 |
| 5,879,362 A | * | 3/1999 | Amann et al. | 606/167 |
| 5,906,053 A | * | 5/1999 | Turner et al. | 30/347 |
| 5,924,206 A | * | 7/1999 | Cote et al. | 30/337 |
| 6,056,764 A | * | 5/2000 | Smith | 606/107 |
| 6,120,518 A | * | 9/2000 | Mark et al. | 606/170 |

FOREIGN PATENT DOCUMENTS

DE    196 52 097 A1    6/1998

* cited by examiner

*Primary Examiner*—Brian L. Casler
*Assistant Examiner*—Cris L. Rodriguez
(74) *Attorney, Agent, or Firm*—Akin Gump Strauss Hauer & Feld, LLP.

(57) ABSTRACT

The stricture scalpel serves for endoscopic use and consists of a blade with a cutter and a stem which is inserted into the distal end of a shank and here is unreleasably connected to this. The shank consists of stainless steel and the blade of a ceramic material.

2 Claims, 1 Drawing Sheet

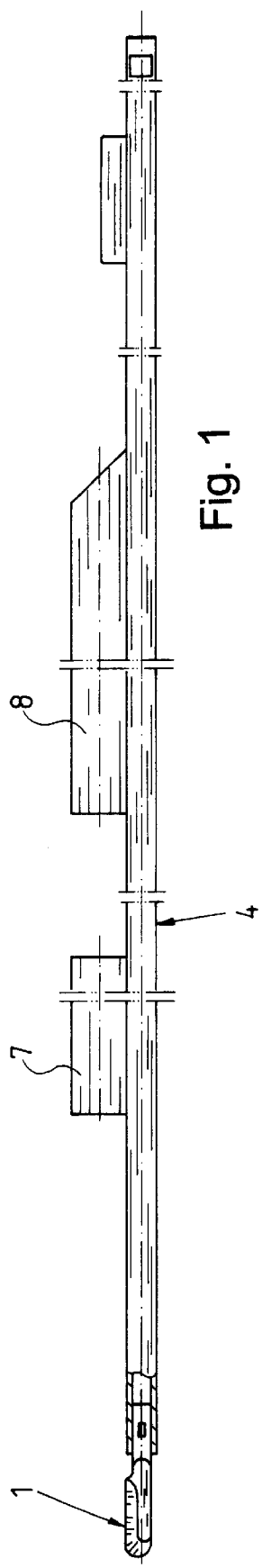
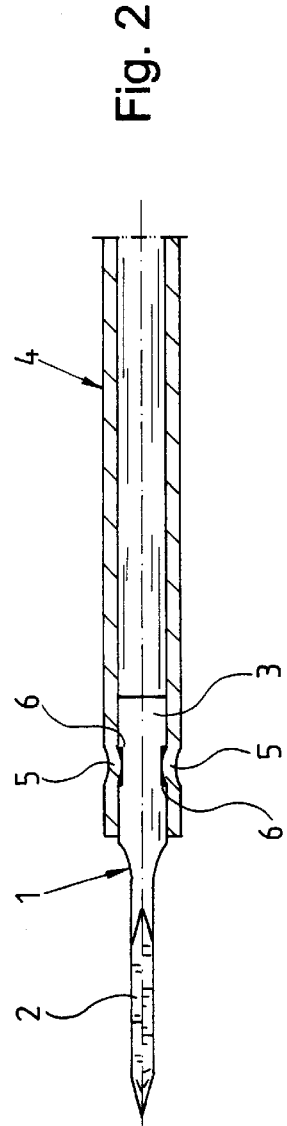
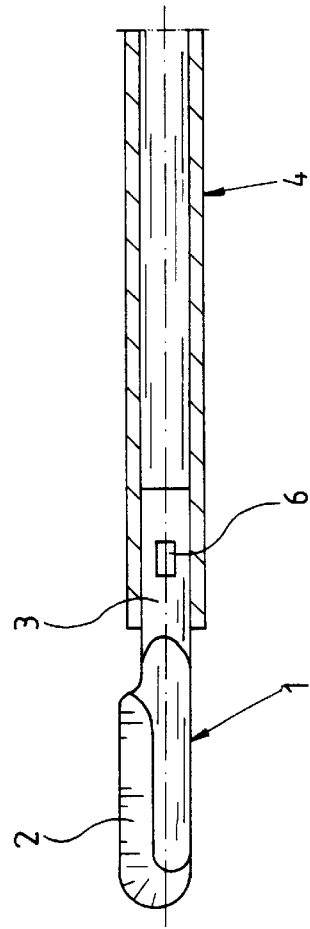
Fig. 1
Fig. 2
Fig. 3

STRICTURE SCALPEL

BACKGROUND OF THE INVENTION

The invention relates to a stricture scalpel for endoscopic use consisting of a blade with a cutter and with a stem which is inserted into the distal end of a shank and here is unreleasably connected to this.

With known scalpels of this type the blade and the relatively long shank to be led through an instrument channel of an endoscope consist of stainless steel so that the scalpel is biocompatible and can also be sterilized. However it has been shown in practice that the cutter mostly becomes blunt already after one to two operations and is no longer usable in order to be able to lead clean smooth cuts e.g. through scars and other relatively solid tissue.

Inasmuch as this is concerned blades coated with ceramic or hard chrome at least in the cutting regions are slightly better, but they however have the disadvantage that the particles of the coating release from the cutter and may remain in the body of the patient.

There are also scalpels (DE 196 52 097 A1) with which the blade and the shank are manufactured as one-piece and as a whole consist of ceramic material and with which the shank forms a handle for holding and guiding the scalpel. Although such scalpels on account of their ceramic blade are suitable for carrying out several operations with a blade remaining sufficiently sharp, they are not usable as stricture scalpels in combination with endoscopes with which the relatively long scalpel shank is to be proximally mechanically connected e.g. with a positive fit, to a working element and must have a small diameter since the diameter of the endoscope shank which is also to accommodate the optics must be kept as small as possible for reasons already known. This requirement above all results with endoscopes which must be introduced through narrow body channels with their distal end to the location of treatment.

With a ceramic scalpel shank or a scalpel as a whole consisting of ceramic material one may not fulfill the demand of an endoscope shank small in diameter since the long thin scalpel shank on account of its brittle material would not resist the mechanical loadings and moreover with an incorrect handling on sterilization or introduction into the endoscope could easily break. This danger of course does not exist with scalpel shanks of stainless steel.

BRIEF SUMMARY OF THE INVENTION

It is the object of the invention to provide a stricture scalpel serving the use with an endoscope, with which the favorable properties of ceramic blade material are used, and otherwise there is a high mechanical strength of the scalpel given a small diameter of its shank.

For achieving the object with the initially mentioned stricture scalpel the shank consists of stainless steel and the blade of ceramic material. By way of this there results a scalpel with a longer life duration of the blade cutter and with the positive mechanical properties as also with scalpels manufactured totally of steel.

Usefully on the circumference of the blade stem there are provided recesses lying opposite one another into which from the outside plastically deformed regions of the scalpel shank engage.

Furthermore the blade is colored black and is reflection-free so that the operator with the cutting procedure is not disturbed by light reflexes which are transmitted proximally from the illuminated treatment location via the endoscope optic. The coloring of the blade material is effected by known methods.

BRIEF DESCRIPTION OF THE DRAWINGS

One embodiment example of the invention is hereinafter described by way of the drawing. There is shown in FIG. 1 a lateral view of a stricture scalpel according to the invention, FIG. 2 the distal end region of the scalpel according to the invention in a plan view of the cutter and FIG. 3 the same distal end region as FIG. 2 in a lateral view of the cutter.

DETAILED DESCRIPTION OF THE INVENTION

The shown scalpel has a ceramic blade 1 with a cutter 2 and a stem 3. This stem is unreleasably inserted in the distal end of a shank 4 of stainless steel which for example consists of a tube section, and which with plastically deformed regions 5 engages into oppositely lying recesses 6 on the stem 3.

The shank 4, at the proximal end thus the right end according to FIG. 1, in the known manner is releasably connected to the working element which is proximally fastened on an endoscope shank and is equipped with a handle on whose actuation the scalpel may be axially adjusted within the endoscope shaft such that the blade cutter 2 projects distally from the endoscope shank, then for leading through tissue sections may be moved to and fro and finally as a whole be moved back into the endoscope shank.

The adjusting movements of the scalpel are effected usually relative to optics which are located stationary in the endoscope shank and via which the operational field may be observed with the cutting procedure and on whose optic tube the scalpel is axially guided. For this purpose on the scalpel shank there are attached sleeves 7 and 8 which encompass the optics tube so that the scalpel with axial movements with the sleeves is slidingly guided on the optic tube.

I claim:

1. A stricture scalpel for endoscopic use comprising an endoscope shank and a blade, the blade having a cutter and a stem for insertion and non-releasable connection into a distal end of the shank, wherein the stem has oppositely lying recesses substantially on its circumference and the shank has plastically deformed regions corresponding to and for engagement in the recesses, the shank comprising stainless steel and the blade comprising ceramic material.

2. The stricture scalpel of claim 1, wherein the blade comprises a material which renders the blade reflection-free.

* * * * *